United States Patent [19]

Dilgren et al.

[11] Patent Number: 4,562,727

[45] Date of Patent: Jan. 7, 1986

[54] OLEFIN SULFONATE-IMPROVED STEAM FOAM DRIVE

[75] Inventors: Richard E. Dilgren, Houston; Kenneth B. Owens, Spring, both of Tex.

[73] Assignee: Shell Oil Company, Houston, Tex.

[21] Appl. No.: 673,645

[22] Filed: Nov. 21, 1984

Related U.S. Application Data

[62] Division of Ser. No. 500,195, Jun. 1, 1983, Pat. No. 4,488,976, which is a division of Ser. No. 247,425, Mar. 25, 1981, Pat. No. 4,393,937.

[51] Int. Cl.⁴ ............................................. G01N 15/00
[52] U.S. Cl. ......................................... 73/60.1; 73/38; 73/432 SD
[58] Field of Search ................... 73/29, 61 R, 60.1, 38, 73/432 SD

[56] References Cited

U.S. PATENT DOCUMENTS

4,148,217 4/1979 Engle .................................. 73/60.1

Primary Examiner—Donald O. Woodiel

[57] ABSTRACT

Steam mobility-reducing capability of an olefin sulfonate-containing surfactant formulation for reducing the mobility of steam of a selected quality within a selected subterranean oil-containing reservoir is tested. Steam of the selected quality and a steam-containing fluid which has substantially the same quality containing the surfactant formulation, an electrolyte and a noncondensable gas upflow through columns of permeable porous mediums containing the reservoir oil. The mass flow rates through the columns are substantially equivalent to a selected flow rate in a near-well portion of the reservoir. Steady-state pressure within the columns are measured and the permeability reducing factor of the surfactant formulation is calculated from the pressure measurements.

2 Claims, 4 Drawing Figures

OLEFIN SULFONATE-IMPROVED STEAM FOAM DRIVE

REFERENCE TO RELATED APPLICATION

This is a division of application Ser. No. 500,195, filed June 1, 1983, now U.S. Pat. No. 4,488,976, issued Dec. 18, 1984, which is a division of application Ser. No. 247,425 filed Mar. 25, 1981, now U.S. Pat. No. 4,393,937, issued July 19, 1983.

BACKGROUND OF THE INVENTION

The invention relates to a steam foam drive process for producing oil from, or displacing oil within, a subterranean reservoir. The invention is particularly suited for use in reservoirs in which stratification due to differences in the absolute permeabilities of individual layers of rocks does not confine a significant portion of injected steam within the layers of highest absolute permeability. The invention also relates to steam-foam-forming compositions which are uniquely effective in a steam foam drive oil displacement process.

In certain respects, this invention is an improvement in the steam-channel-expanding steam foam drive process of U.S. Pat. No. 4,086,964. The disclosures in and references pertinent to the U.S. Pat. No. 4,086,964 (hereinafter referred to as the '964 patent) are incorporated herein by cross-reference.

The present invention is particularly useful in an oil producing process of the type described in the '964 patent. In the '964 process steam is injected into, and fluid is produced from, horizontally spaced locations within a portion of an oil reservoir in which the disposition of a steam flow path is determined by gravity and/or oil distribution, rather than being substantially confined within layers of relatively high absolute permeability. After a steam channel has been formed and extended until a steam breakthrough into a production location is at least substantially imminent, the composition of the fluid being injected is changed from steam to a steam-foam-forming mixture. The composition of the mixture is correlated with the properties of the rocks and the fluids in the reservoir so that the pressure required to inject the mixture and move it through the steam channel exceeds that required for steam alone but is less than the reservoir fracturing pressure. The composition and rate of injecting the mixture is subsequently adjusted to the extent required to maintain a flow of steam foam within the channel at a relatively high pressure gradient at which the oil-displacing and channel-expanding effects are significantly greater than those provided by the steam alone—without plugging the channel. Oil is recovered from the fluid produced from the reservoir.

As used herein the following terms have the following meanings: "Steam Foam" refers to a foam and/or gas-liquid dispersion which (a) is capable of both reducing the effective mobility, or ease with which a fluid containing such a foam or dispersion will flow within a permeable porous medium and (b) has a gas-phase which is mostly dry (or dry saturated) steam. "Mobility" or "permeability" refers to an effective mobility or ease of flow of fluid within a permeable porous medium. A "permeability reduction" or "mobility reduction" refers to reducing the ease of such a fluid flow due to an increase in the effective viscosity of the fluid and/or a decrease in the effective permeability of the porous medium. A reduction in such a mobility or permeability can be detected and/or determined by measuring differences in internal pressures within a column of permeable porous material during a steady state flow of fluid through a column of such material. "Steam quality" as used regarding any steam-containing fluid refers to the weight percent of the water in that fluid which is in the vapor phase of the fluid at the boiling temperature of that water at the pressure of the fluid. For example: in a monocomponent steam-containing fluid which consists entirely of water and has a steam quality of 50%, one-half of the weight of the water is in the vapor phase; and, in a multicomponent steam-containing fluid which contains nitrogen in the vapor phase and dissolved or dispersed surfactant and electrolyte in the liquid phase and has a steam quality of 50%, one-half the weight of the weight of the water in the multi-component steam-containing fluid is in the vapor phase. Thus, the steam quality of a steam-containing fluid can be calculated as, for example, 100 times the mass (or mass flow rate) of the water vapor in that fluid divided by the sum of the mass (or mass flow rate) of both the water vapor and the liquid water in that fluid. "Steam-foam-forming mixture" (or composition) refers to a steam-containing mixture of steam and aqueous liquid solution or dispersion of surfactant, with some, all, or none, of the steam being present in the gas phase of a steam foam.

SUMMARY OF THE INVENTION

The present invention relates to an improved process for displacing oil by flowing a steam-foam-forming mixture into the pores of an oil-containing subterranean reservoir. The improvement is provided by using a steam-foam-forming mixture consisting essentially of steam mixed with a surfactant component comprising in substantial part olefin sulfonate. In a preferred embodiment the present olefin sulfonate-containing steam-foam-forming mixture includes an aqueous solution of electrolyte and, more preferably, also includes a substantially noncondensable gas; with each of the surfactant, electrolyte and gas components being present in proportions effective for steam-foam-formation in the presence of the reservoir oil. The present invention also relates to the olefin sulfonate-containing steam-foam-forming mixtures which are described herein.

The present invention is useful where it is desirable to produce oil from or displace oil within the pores of a subterranean reservoir. For example, the invention can be used to move oil or an emulsion of oil and water through the reservoir and thus away from a well borehole in a well-cleaning type of operation, and/or to displace oil into a producing location in an oil-recovery operation.

DESCRIPTION OF THE INVENTION

The present invention is, at least in part, premised on a discovery that unobvious and beneficial advantages are provided by the presently described olefin sulfonate surfactant-containing steam-foam-forming compositions. For example, where a steam-foam-forming mixture contains such a surfactant, a noncondensable gas and an electrolyte in proportions near optimum for foam formation, the present surfactant components provide exceptionally strong steam foams having mobilities many times less than those of the foam-free steam or a mixture of that steam with the other components except for the surfactant. In addition, the presently described surfactant components, when used as the surfactant components of steam-foam-forming mixtures, provide significant reductions in the mobilities of the steams at concentrations which are much less than those required for equal mobility reductions by the surfactants which were previously considered to be the best available for such a purpose. The use of the present olefin sulfonate surfactant components appears to involve no problems with respect to thermal and hydrolytic stability. No chemical or physical deterioration has been detectable in either the present olefin sulfonate surfactants or the previously used alkaryl sulfonate surfactants that were recovered along with the fluids produced during productions of oil from subterranean reservoirs. In each of those types of sulfonate surfactants the sulfur atoms of the sulfonate groups are bonded directly to carbon atoms. The surfactants which were recovered and tested during the production of oil had travelled through the reservoirs at steam temperatures for significant times and distances.

The present olefin sulfonate-containing steam foams have been found to represent a substantial improvement in oil-displacing efficiency over foams based on the alkaryl sulfonates e.g., dodecylbenzene sulfonates. The alkaryl sulfonates were heretofore particularly suggested as superior surfactants for steam-foam service; for instance, in the process of the '964 patent and also in the related process described in *Progress Review No. 22* (DOE/BETC-80/2), *Contracts for Field Projects and Supporting Research on Enhanced Oil Recovery and Improved Drilling Technology,* published for the first quarter of 1980 by the Bartlesville Energy Technology Center of the U.S. Department of Energy, p. 107–108, *Kern Front Field Steam Drive with Ancillary Material.*

The present invention further relates to novel olefin sulfonate, steam, noncondensable gas and electrolyte-containing compositions preferred for use in an oil-displacing and/or producing process. Of particular interest in this respect are steam-foam-forming compositions consisting essentially of (a) water, which is present in the composition, at a temperature substantially equalling its boiling temperature, at the pressure on the composition, in both a liquid phase and a vapor phase of a steam of at least about 30% quality; (b) a surfactant component present in the liquid phase of the composition in an amount between about 0.01 and 5 percent by weight, calculated on the weight of the liquid phase, said surfactant component comprising in substantial part olefin sulfonate; (c) an electrolyte present in the liquid phase of the composition in an amount between about 0.1 percent by weight (calculated on the weight of the liquid phase) and an amount tending to partition the surfactant into a separate liquid phase; and (d) a noncondensable gas present in the vapor phase in an amount between about 0.0003 and 0.3 percent by mol, calculated on total mols in the vapor phase.

Illustrative of the olefin sulfonate surfactants suitably employed in steam-foam drive processes of enhanced performance, according to the invention, are the olefin sulfonates obtained by hydrolysis and neutralization of the product of reacting sulfur trioxide with olefins having a carbon number in the range from about 10 to 24, inclusive. Particularly suitable for purposes of the invention is an olefin sulfonate derived from substantially linear alpha-olefins in the $C_{14}$ to $C_{20}$, and, most particularly, those derived from linear alpha-olefins in the $C_{16}$ to $C_{18}$ range.

Although relevant properties of particular olefin sulfonates vary due to variations in their chemical composition, e.g., according to carbon number and configuration of the olefin from which they are prepared, sulfonation reaction conditions, etc., and although, as indicated in the '964 patent, different reservoir oils have different debilitating effects on the strength of a steam foam, specific olefin sulfonates or olefin sulfonate-containing steam-foam-forming compositions from the class herein described as suitable for the present invention may be readily matched to optimum service in a given reservoir. This is preferably done by testing their affect on the mobility of a steam-containing fluid having the steam quality selected for use in the reservoir in the presence of the reservoir oil.

Such tests are preferably conducted by flowing steam-containing fluids vertically upward through an oil-containing sand pack. The permeability of the sand pack and foam-debilitating properties of the oil in the sand pack should be at least substantially equivalent to those of the reservoir to be treated. Comparisons are made of the mobility of the steam-containing fluid with and without the surfactant component. The mobility is indicated by the substantially steady-state pressure drop between a pair of points located between the inlet and outlet portions of the sand pack in positions which are substantially free of end effects on the pressures.

LABORATORY TESTS OF STEAM MOBILITY

Figures 1, 2:
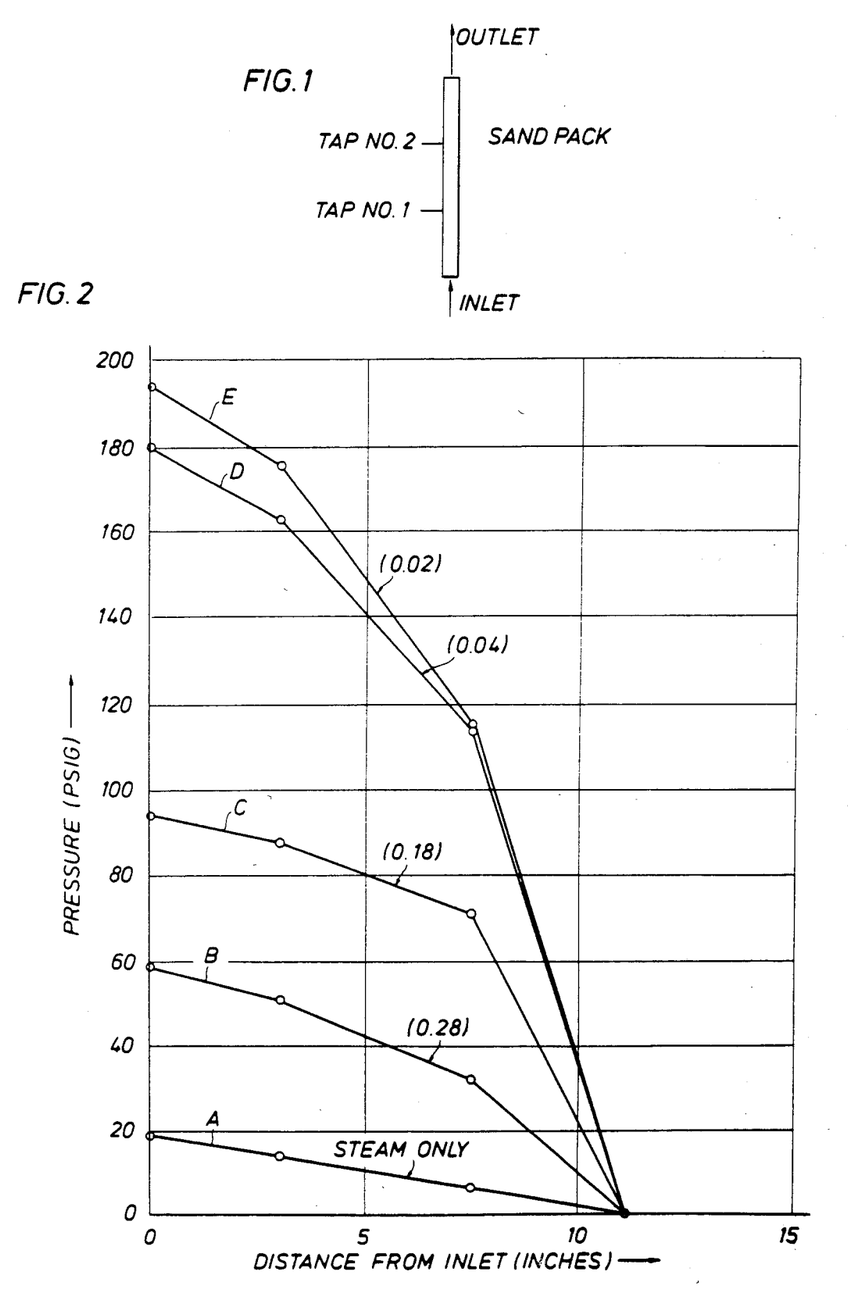
FIG. 1 is a schematic illustration of an apparatus suitable for testing the steam mobility-reducing capability of a given steam foam forming mixture.
FIGS. 2 and 3 are plots of the variations in internal fluid pressure with distance along a sand pack as steam or steam-foam-forming mixture is flowed through the pack.

FIG. 1 shows a sand pack test apparatus (which can be made of currently available apparatus components). The illustrated apparatus consists of a cylindrical sand pack of dimensions such as 1.25 inches in diameter by 11 inches long. Such a pack is preferably arranged for an upward flow of fluid from an inlet at the bottom to an outlet at the top. The pack is preferably provided with at least two pressure taps, at locations such as Taps 1 and 2 on the Figure, which are positioned so as to divide the pack approximately into thirds. Such an apparatus can utilize a column of substantially any permeable porous material, such as a pack, core, frit, or the like, which is capable of providing an adequately realistic laboratory model of a subterranean reservoir.

At the inlet end, the sand pack or equivalent column of permeable material is preferably arranged to receive separate streams of steam, a noncondensable gas such as nitrogen, and one or more aqueous liquid solutions or dispersions containing a surfactant to be tested and/or a dissolved or dispersed electrolyte. Some or all of those components are injected at constant mass flow rates proportioned so that steam of a selected quality, or a selected steam-containing fluid or composition, or a steam-foam-forming mixture of a selected steam quality can be injected and will be substantially homogeneous substantially as soon as it enters the face of the sand pack. For example, pumps such as the Beckman Accu-Flo positive displacement pumps can be used to inject liquids such as the water pumped through a steam generator (e.g., a coil of 1/16 inch O.D. stainless steel tubing), an aqueous solution of the electrolyte and an aqueous liquid containing the surfactant. A tank of pressurized nitrogen can be used to inject noncondensable gas. The tank pressure is reduced to the desired value, the flow rate is measured by a rotometer such as a Fisher & Porter Company rotometer and is controlled by a constant flow regulator and a control valve which are located downstream of the rotometer.

A steam-containing fluid of the steam quality to be used in a steam or steam-foam-forming mixture to be injected into a reservoir is preferably compared with and without a surfactant component by measuring pressure gradients formed within a sand pack (or equivalent permeable column) during flows through the same or an equivalent sand pack at the same substantially constant mass flow rate. The flow rate used in such tests is preferably within the range of from about 2 to 4 ml/min (or g/min) of water, where about half of the water is dry steam and the remainder is an aqueous liquid containing the surfactant and electrolyte. The gas-phase of such a steam preferably contains a small proportion of noncondensable gas. However, laboratory and field tests have shown that the proportion of noncondensable gas which provides a significant effect in a field operation tends to be too small to be significant in laboratory tests of steam-containing fluids which are free of a surfactant component. In general, the rate at which the steam-containing fluid is flowed through the pores of the sand pack is preferably substantially equivalent to the flow rate to be utilized in flowing such a fluid through the near-well portion of a reservoir. The pressure measurements are preferably made by means of pressure transducers at least substantially equivalent to those available from Valedyne Engineering Corporation.

Numerous tests have been made of different steam-foam-forming mixtures using such packs composed of a reservoir sand such as an Ottawa sand containing Kern River crude oil and having a high permeability, such as 4 darcys. The pressures were measured with measuring taps (such as piezoelectric devices) installed at the inlet and the interior locations, such as Taps 1 and 2. The results of such tests have proven to be very consistent with the results obtained in field tests.

In such laboratory tests, the steam-foam-forming components were injected at constant mass rates until substantially steady-state pressures were obtained at the inlet and the internal taps. The steady-state pressures at the internal taps were used with equations for isothermal single phase flow of an ideal gas to calculate the effective mobility (or effective permeability) to the steam by itself and mixed with the foam-forming surfactant component. The ratio of the latter to the permeability to steam in the absence of the surfactant component can be termed "the permeability reduction factor". The smaller this factor, the stronger the steam foam and the lower the mobility of the steam-foam-forming mixture.

The laboratory tests are preferably conducted in the presence of the reservoir oil or an oil substantially equivalent to it with respect to viscosity and steam-foam-debilitating properties. In a preferred procedure the packs prepared by flooding them with a given oil at an elevated temperature, such as 210° F., to provide oil saturations in the order of 70 to 80% of the pack pore volume. Hot water floods, usually amounting to 9 to 10 pack pore volumes, are conducted to reduce the oil saturations to hot water residuals of about 60 to 70%. The hot water floods are followed by wet steam drive using about 8 or 9 volumes of water converted to steam of a selected quality, such as 50%. This reduces the oil saturation to a range such as 30 to 50% (at which some oil can be produced by a wet steam drive but is an amount which is small in proportion to the amount of drive fluid).

FIG. 2 illustrates the results of comparative tests with steam and various steam-foam-forming mixtures in sand packs prepared as described above. The figure shows the variation of the pressure in pounds per square inch with distance from the pack inlet as measured at the inlet, Taps 1 and 2, and the outlet. Curve A relates to using a mixture of 50% quality steam. The pressure performance of such a steam has been found to be substantially identical with that of a steam which has the same quality but has a gas-phase that contains 0.006 mole fraction of nitrogen gas.

Curve B relates to using a steam-containing fluid having a steam quality of 50% and a water-phase which contains 1% by weight sodium chloride and 0.5% by weight of surfactant. In the Curve B test, the surfactant was a branched side-chain dodecylbenzene sodium sulfonate available from Witco Chemical Company as Witco EXP 4498-43B surfactant.

Curve C relates to using the mixture used for Curve B except that the surfactant was a branched side-chain dodecylbenzene sodium sulfonate available from Alcolac, Incorporated under the trademark Siponate DS-10 surfactant.

In the tests represented by Curves D and E the formulation was the same as those used in the tests represented by Curves B and C except that the sulfonate components were olefin sulfonates, in accordance with the present invention. Curve D relates to the use of the Alcolac Siponate alpha-olefin sulfonate product A-168, obtained via the sulfonation, hydrolysis, and neutralization of an olefin mixture characterized in terms of carbon number as about 55% $C_{16}$ and 45% $C_{18}$, and further characterized in terms of molecular structure as about 70% linear terminal, about 20% branched terminal, and about 10% linear internal. Curve E relates to the use of an alpha-olefin sulfonate prepared by Stepan Chemical Company via the sulfonation, hydrolysis, and neutralization of an olefin mixture characterized as about 55% $C_{16}$ and about 42% $C_{18}$, and further characterized as about 94% linear terminal, about 3% branched terminal, and about 2% linear internal.

An alkaryl sulfonate such as Siponate DS-10 dodecylbenzene sulfonate is described in the '964 patent as a particularly preferred surfactant for use in that steam-channel-expanding steam foam drive. The greatly improved steam permeability reduction performance of the presently described olefin sulfonate-containing surfactant component is shown in FIG. 2.

The greatly improved performance is also dramatically illustrated by the permeability reduction factors, which are the numbers in parentheses on the Curves in FIG. 2. The smaller this factor, the stronger and more effective is the steam foam. The permeability reduction factor for the olefin sulfonate surfactant used in the test represented by Curve D is less than one-fourth of that for the previously preferred alkaryl sulfonate surfactant, and thus, the olefin sulfonate used in the Curve D test is more than four times more effective as a surfactant component of a steam-foam-forming composition. A comparison of the Curves A and D show that when steam is foamed with that olefin sulfonate surfactant the steam mobility is reduced to about one-twenty-fifth of the mobility in the absence of any surfactant. And, such a comparison of Curves A and E shows an even greater reduction, to one-fiftieth of the mobility in the absence of surfactant.

PERMEABILITY REDUCTION FACTOR VERIFICATION TESTS

Steam foam formulations which result in significant mobility reductions will display a common characteristic in the 12-inch sand packs. The greater portion of the steady-state pressure drop occurs between the downstream pressure tap and the outflow end of the sand pack. This effect is well illustrated by FIG. 2.

To further examine this effect, a sand pack was prepared in a steel tube of nominal 18-inch length. This longer tube was equipped with pressure taps located to divide the tube into quarters, and an additional three pressure taps were installed in the downstream quarter. A Kern River oil saturation of 30% pore volume was established in the sand pack. A steam-foam-forming mixture which was equivalent to a steam of substantially 50% quality and contained 0.5% weight, Witco Exp. 4498-43B surfactant, 3% weight NaCl, and 0.006 mole fraction nitrogen was injected until steady-state was achieved.

Figures 3, 4:
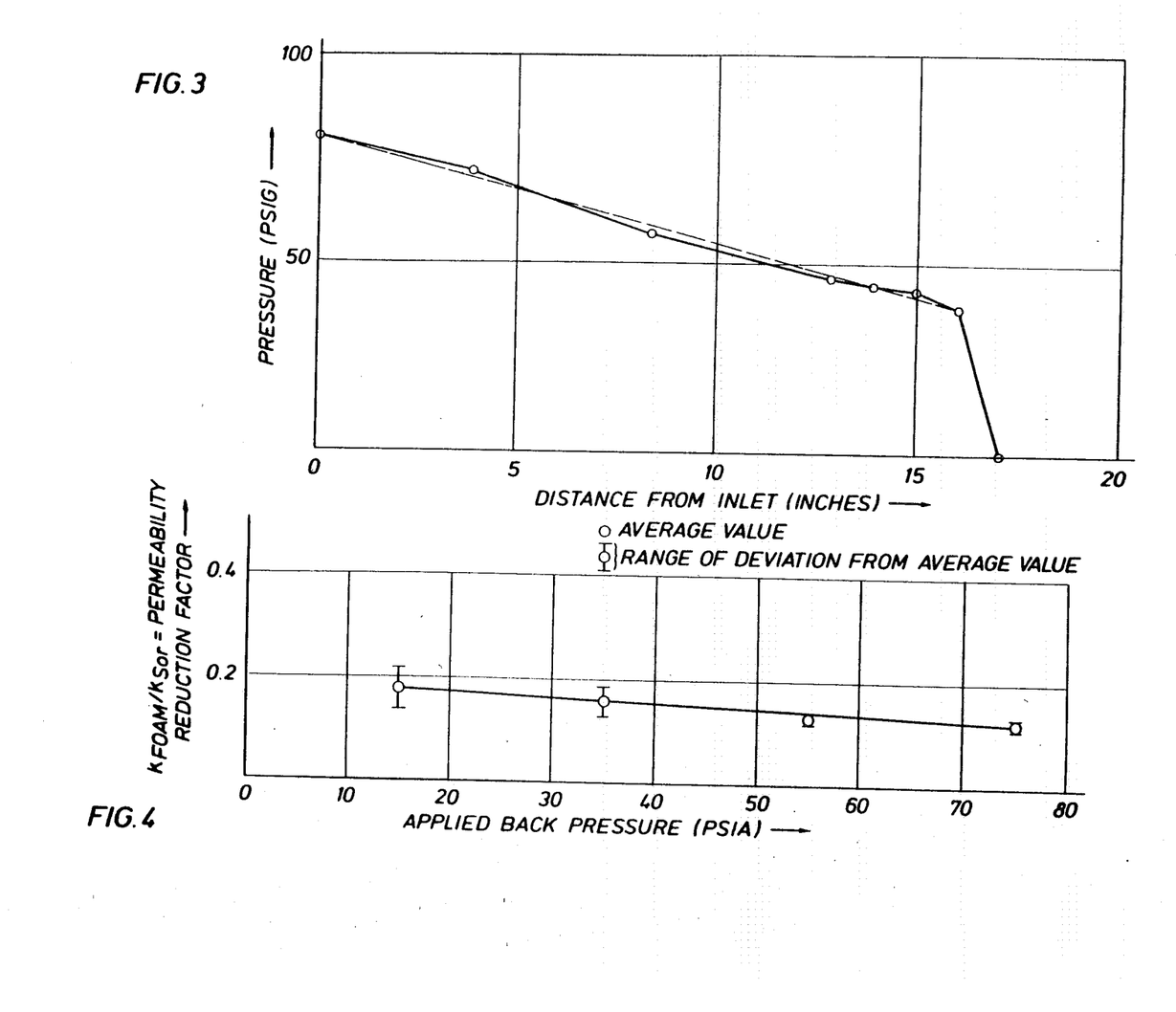
FIG. 4 is a plot of permeability reduction factor variation with increases in backpressure.

The steady-state pressure profile is shown in FIG. 3. Solid lines connect the experimental points and the dashed line represents a linear pressure drop from the inlet to the last downstream pressure tap. A rather severe end effect, associated the flow of steam foam through the very last portion of the sand pack and/or the frit used to contain the sand, is obvious.

At the end of the experiment the steel frit was removed from the end of the sand pack and its permeability determined, both "as was" and after cleaning. Permeabilities were 8 and 11 darcys, respectively; these compare with the 4 darcy permeability of the sand pack itself. The inordinate pressure drop at the end of the sand pack and/or through the steel frit, although not yet understood, appears to be an artifact of the sand pack flow experiment as is, for example, the familiar capillary endeffect. Thus, the use of steady state pressures at the interior pressure taps to calculate permeability reduction factors seems to be justified.

One possible explanation for the large pressure drop at the end of the pack involves flashing of the liquid phase of the steam-containing fluid. Such flashing could lead to three contributing effects. First, the kinematic viscosity of steam is greater than that of liquid water, thus enhancing the pressure drop relative to lower quality steam. Second, complete flashing would result in deposition of solid salt in the end of the sand pack and/or the stainless steel frit. Partial plugging by solid salt could also contribute to the excessive pressure drop.

At the end of the experiment, the sand was scooped out in separate sections. The individual sections were dried, triturated with known amounts of water, and the water extracts were analyzed for chloride. The results indicated no significant salt accumulation in the downstream end of the sand pack. Furthermore, the frit itself contained only 0.005 mg. of salt. To put these numbers in perspective, a total of 20,250 mg. of salt was injected in the steam foam formulation during the course of the experiment. Apparently complete flashing does not occur and enough liquid water is present to keep the salt in solution. To the extent that some flashing does occur, a third factor could contribute to the large pressure gradient. Flashing would concentrate the surfactant in the remaining liquid water. In previous tests increasing surfactant concentration has been shown to enhance the end effect.

All steam foam experiments performed to date have had the downstream end of the sand pack at atmospheric pressure. In field application, however, the steam foam experiences varying degrees of effective back pressure. During the initial steam foam pilot tests described in the '964 patent, for example, bottom hole injection pressure for steam foam was often about 110 psig while pressure at the producing sand face was estimated to be about 5 psig.

This prompted a series of experiments to determine the sensitivity of mobility reduction, as measured by permeability reduction factor, to applied back pressure. Sand packs of 12-inch nominal length were employed, and steam foam injection was initiated at a Kern River oil saturation of about 30% pore volume. The same steam foam formulation was used as for the 18-inch sand pack experiment described above. Back pressure was maintained by inserting in the production line a fine metering valve which was arranged to accommodate the simultaneous flow of steam, liquid water, and heavy oil.

Steam foam drive experiments were performed in duplicate at four levels of back pressure ranging from atmospheric to 75 psia. Permeability reduction factors are plotted as a function of back pressure in FIG. 4. Steam foam mobility reduction appears to be relatively insensitive to applied back pressure. If anything, there may be a mild bias towards reduced mobility with higher applied back pressure. Thus the presently described procedure for screening steam foam formulations, i.e., with the downstream end of the sand pack at atmospheric pressure can be viewed as yielding relatively conservative estimates of mobility reduction.

FIELD TEST I (PRIOR ART)

The "Field Test II" with Siponate DS-10 surfactant described in the '964 patent was expanded from a single 5-spot pattern to four contiguous 5-spot patterns and repeated.

The surfactant used in the expanded pattern was the previously used dodecylbenzene sulfonate (Siponate DS-10) surfactant. The steam-foam-forming mixture which was injected had a steam quality of about 50%. That mixture contained within its liquid-phase about 0.5% weight surfactant and 4.0% weight sodium chloride. The gas-phase of the mixture contained about 0.006 mole fraction of nitrogen.

The steam-foam-forming mixture was initially injected into only three of the injection wells. In those wells, the bottom hole injection pressures increased rapidly from about 20–30 psig to about 120–125 psig, and stayed within the latter range.

In the fourth injection well, the injection was started with only the steam and surfactant. This caused a pressure increase from about 25 psig to 45 psig. The formulation was then changed to include 1.0% sodium chloride in the liquid phase—which caused little change in bottom hole injection pressure. When nitrogen was introduced into the fourth injection well at the rate of 3.6 standard cubic feet per minute, the bottom hole injection pressure climbed rapidly to about an average pressure of 110 psig. The sodium chloride concentration of the steam-foam-forming mixture entering the fourth injector was then increased to 4.0%, (making the concentration of all components the same as that employed in the other three injection wells) and the bottom hole injection pressures within the pattern maintained an average value of about 120 to 130 psig.

FIELD TEST II (PRESENT INVENTION)

The steam-foam-forming mixture being injected into the four test wells was subsequently modified by switching from the sodium dodecylbenzene sulfonate DS-10 surfactant to an olefin sulfonate surfactant, in accordance with the present invention. The use of the olefin sulfonate surfactant component (without otherwise altering the composition of the steam-foam-forming mixture being injected) increased the average value of the bottom hole injection pressures to about 160–170 psig. The changeover also caused an increase in the average daily rate of oil production. The DS-10 surfactant (prior art) caused an increase of from about 135 BDO to 240 BDO and the A-168 surfactant (present invention) caused a further increase of from about 240 barrels per day of oil (BDO) to a value of about 363 BDO, which is still increasing.

During the startups of the injections of the DS-10 and A-168 surfactants, prior to the inclusion of the nitrogen and sodium chloride components of the steam-foam-forming mixtures, the following observations were made regarding the bottomhole injection pressures. With the DS-10 surfactant (prior art), during the first three days the pressure increased from about 25 to about 45 psig.

The A-168 surfactant (present invention) was initially injected (without nitrogen or sodium chloride) into a well in which the injection pressure had been increased to about 140 psig by a prior injection of the DS-10 surfactant with nitrogen and sodium chloride. During the first three days of injecting the mixture of only steam and the A-168 surfactant, the bottomhole injection pressure decreased to about 118 psig. Part of the decrease was due, of course, to the lower foam strength of the gas and electrolyte-free mixture. Part of the decrease was also due to a four-hour well shutdown. But within two more days the pressure had stabilized at about 125 psig—was almost triple the value obtained by the similarly gas-and-electrolyte-free steam-foam-forming fluid containing the DS-10 surfactant. And, although the injection pressure fluctuated due to additional shutdowns, the near 125 psig value was maintained until it was increased to the 160–170 psig range by the inclusion of the gas and electrolyte components of a preferred steam-foam-forming mixture of the present invention.

COMPOSITIONS AND PROCEDURES SUITABLE FOR USE IN THE PRESENT INVENTION

For purposes of the present invention, the surfactant component of the steam-foam-forming mixture is necessarily comprised in substantial part of olefin sulfonate, a known material which has heretofore found commercial utility, for example, in detergent formulations for industrial, household and personal care application.

A class of olefin sulfonates very suitable for use in the present invention is that derived from a particular class of olefins, which may be defined for present purposes in terms of the configuration and number of carbon atoms in their molecular structure. (In the chemical arts, olefin sulfonates are commonly described in terms of the olefins from which they can be prepared). These olefins have a carbon number in the range from about 10 to 24, preferably in the range from about 14 to 22, and more preferably in the range from about 15 to 20. It is considered most particularly preferred that at least about 50% of the olefin sulfonate content of the surfactant component of the steam-foam-forming mixture be derived from olefins in the $C_{16}$ to $C_{18}$ range.

In terms of molecular structure, these olefins are aliphatic, (or acyclic) and suitably either linear or branched or alicyclic. In preferred embodiments, however, it is desirable that no more than about 50% of the olefin molecules have branched carbon chains. Preferably, at least about 75%, more preferably at least about 85%, and most preferably at least about 90% of the olefin molecules in the $C_{10}$ to $C_{24}$ range are of a linear (normal) configuration. Either alpha or internal olefins are considered suitable for use in the invention. Preference in this regard may be generally stated for olefins which are in major part alpha-olefins while olefins in which less than 25% of the molecules are internal olefins are particularly preferred. Most preferred for purposes of derivation of olefin sulfonates for use in the invention are olefins in which at least about 90% of the molecules are alpha-olefins.

In exemplification of specific ones of these olefins which are suitable for use in synthesizing sulfonates having utility as surfactant components in the process of the present invention, mention may be made of olefins prepared according to a variety of known methods and available from a number of commercial sources. Particularly suitable olefins of high linear alpha-olefin content, manufactured by the cracking of paraffin wax, are available as the Chevron Alpha Olefin product series, trademark of and sold by Chevron Chemical. Commercial production of olefins in the $C_{10}$ to $C_{24}$ range is more commonly accomplished by oligomerization of ethylene utilizing Ziegler catalysts. Alpha-olefin rich products obtained in this manner are marketed in the United States by Gulf Oil Chemicals Company under the trademark Gulfene and by Ethyl Corporation as Ethyl Alpha-Olefins. In comparison to other commercial alpha-olefins the Ethyl product is relatively high in its content of branched vinylidene olefins (about 20%) and internal olefins (about 10%). Good results for the practice of the invention have been obtained utilizing sulfonates of the Ethyl olefin products, particularly sulfonates of $C_{16}$ and $C_{18}$ alpha-olefin mixtures as described above, regarding Curve D of FIG. 2. The use of sulfonates derived from the Gulf-produced alpha-olefin products or the Neodene alpha-olefins, trademark of and sold by Shell Chemical Company, is, however, particularly preferred, in part for their linear structure and high alpha-olefin content, i.e., greater than 90% in each case. The Neodene alpha-olefins are prepared by ethylene oligomerization, generally according to the teachings of U.S. Pat. Nos. 3,676,523; 3,686,351; 3,737,475; 3,825,615 and 4,020,121. Products having a high content of internal olefins in the $C_{10}$ to $C_{24}$ range are also commercially manufactured, for instance, by the chlorination-dehydrochlorination of paraffins or by paraffin dehydrogenation, and can also be prepared by isomerization of alpha-olefins. Internal-olefin-rich products are manufactured and sold, for example, by Shell Chemical Company and by Liquichemica Company.

For preparation of olefin sulfonates, the olefins as described above are subjected to reaction with sulfur trioxide. The term "sulfur trioxide" as used in the present specification and claims is intended to include any compounds or complexes which contain or yield $SO_3$ for a sulfonation reaction as well as $SO_3$ per se. This reaction may be conducted according to methods well known in the chemical arts, typically by contact of a flow of dilute $SO_3$ vapor with a thin film of liquid olefin at a temperature in the range of about 40° to 120° F. The reaction between the $SO_3$ and the olefin yields an intermediate, believed to be in the nature of a sultone, which is subsequently hydrolyzed by reaction with water and neutralized by reaction with a base, preferably an alkali or alkaline earth metal hydroxide, oxide, or carbonate. In illustration of the composition of the typical olefin sulfonate product, if the olefin is of high alpha-olefin content and the base utilized is sodium hydroxide, the sulfonation, hydrolysis, and neutralization reactions yield a complex mixture of sulfonated compounds principally comprising alkene sulfonic acid sodium salts, hydroxy-alkane sulfonic acid sodium salts and alkene disulfonic acid disodium salts. Although the composition of the sulfonate product varies somewhat depending on a number of factors, particularly the nature of the olefin and the sulfonation reaction conditions, these three principal components are usually present in the product in quantities of about 50 to 70% by weight (%w), 20 to 40 %w, and 5 to 15 %w, respectively. This sulfonate product would also contain other sulfonated compounds, usually in lesser amount, particularly the higher order alkene sulfonate and hydroxyalkane sulfonate sodium salts.

The specific composition of olefin sulfonates prepared as described above (and also, for instance, the methods used for sulfonation, hydrolysis, and neutralization of the specified olefins) have not been found to be a critical factor to the performance of the surfactant in the steam foam drive process of this invention. In this regard, it is observed that factors which have conventionally governed the choice of sulfonation conditions, e.g., product color, clarity, odor, etc., do not carry the same weight in the preparation of olefin sulfonates for purposes of use in the invention that they have been accorded in detergent manufacture. Consequently, reaction conditions outisde of those heretofore considered desirable for olefin sulfonation are still suitably applied in the preparation of surfactant components suitable for use in the steam-foam-forming mixture.

For purposes related to maintaining product stability, conventional manufacture typically yields a dilute solution of the olefin sulfonates, for instance, a 30%w solution in water. Such dilute solutions may be directly applied to the preparation of steam-foam-forming mixtures for purposes of this invention.

Suitable olefin sulfonates, generally prepared by methods such as described above, are themselves commercially available products. Representative of such olefin sulfonate materials are those within the scope of current specifications for products sold under the trade names Allfoam (Chemithon Corp.); BioTerge AS40 (Stepan Chemical Co.); Conco AOS-40 and Conco AOS-90F (Continental Chemical Co.); Polystep A-18 (Stepan Chemical Co.); Sterling AOS (Canada Packers, Ltd.); Sulfotex AOS (Textilona Division of Henkel, Inc.); Sulframin AOS 14-16 and Sulframin AOS 90 Flakes (Witco Chemical Corp.); Ultrawet AOK (Arco Chemical Co.); Elfan OS 46 (Akzo Chemie); Hostapur OS (Hoechst AG); and Lipolan 327N, Lipolan 1400, Lipolan AO, Lipolan G, and Soft Detergent 95 (Lion Corp.). Apart from limitations which relate to identification of the olefin utilized for preparation of the sulfonate, such commerical specifications generally relate to the product's general appearance, color, odor, inorganic salt content, free (unsulfonated) oil content, and pH (alkaline).

As indicated in the '964 patent, the strength of the foam formed by a steam-foam-forming composition tends to increase with increases in the proportion of the surfactant and/or electrolyte components of the composition. Also, as is true with most surfactant-containing compositions, there tends to be an optimum ratio of surfactant and electrolyte components at which the surface-activity of the composition is maximized. These tendencies are also generally applicable to the present olefin sulfonate-containing steam-foam-forming compositions.

However, although the present compositions are generally similar to those described in the '964 patent, the present compositions are significantly different in numerous respects. Their surfactant component is unique. It comprises, in substantial part, olefin sulfonates. Because of this, the present compositions are capable of forming steam-foams of significantly greater strength. In general, it is preferred that a steam-foam-forming composition of the present invention form a steam-foam capable of providing a permeability reduction factor lower than about 0.18, and more preferably, lower than about 0.10 (thus reducing the effective mobility of the steam to less than about 1/6th and more preferably, to less than about 1/10th of the mobility it would have within a permeable porous medium in the absence of the surfactant).

It has now been discovered that the suitability of a particular olefin sulfonate-containing steam-foam-forming mixture for use in a steam of a selected quality in a selected oil-containing reservoir can be determined relatively easily and reliably. Such a mixture is generally suitable when its surfactant component has a chemical composition making it capable of providing a permeability reduction factor of less than about 0.18 in a steam-containing fluid which has the selected steam quality, contains proportions of electrolyte and noncondensable gas which are at least near optimum for steam-foam-forming surface activity and is upflowed through a column of permeable porous material containing the reservoir oil (or an oil which is equivalent to it with respect to viscosity and steam-foam-debilitating properties).

Where the surfactant component of the present steam-foam-forming mixtures or compositions contains one or more surfactants other than the present specified olefin sulfonate surfactant, the proportion of the olefin sulfonate should be large enough so that the composition is capable of providing a steam-foam strength (e.g., as indicated by a permeability reduction factor) exceeding that provided by a similar composition in which the surfactant component consists of only said other surfactant.

Particularly in situations in which the mobility of a steam-foam formed in accordance with the present invention might be too low in view of one or more conditions such as a relatively low reservoir permeability, a shallow and/or otherwise relatively easily fractured reservoir, a limited capacity for generating pressurized steam, or the like, the concentration of the olefin sulfonate-containing surfactant component can be reduced to the extent required to provide an effective mobility and resultant pressure gradient suitable for that situation. As will be apparent to those skilled in the art, the effects of a particular reservoir permeability and/or oil viscosity property can readily be determined, preferably by a flow test of the type described above for measuring the permeability reduction factor.

Permeability reduction factors determined in accordance with the presently described procedures have been found to be relatively accurately indicative of the behavior of the present type of steam-foam-forming compositions in subterranean reservoirs. By means of such tests determinations can be made of the proportions of substantially noncondensable gas, surfactant and electrolyte components which are needed in a steam of the quality to be used in order to provide the desired pressure gradient in the reservoir to be treated. Of course, such tests can also be used to determine the proportion of the surfactant component to be used where the gas and/or electrolyte is to be omitted.

The steam used in the present process and/or compositions can be generated and supplied in the form of substantially any dry, wet, superheated, or low grade steam in which the steam condensate and/or liquid components are compatible with, and do not inhibit, the foam-forming properties of the foam-forming components of a steam-foam-forming mixture of the present invention. It is preferable that the steam quality of the steam as generated and/or amount of aqueous liquid with which it is mixed be such that the steam quality of the resulting mixture is from about 10 to 90%, and more preferably, from about 30 to 80%. In this regard, the desired steam-foam is advantageously prepared by mixing the steam with aqueous solution(s) of the surfactant component and optionally, an electrolyte. The water content of these aqueous solutions must, of course, be taken into account in determining the steam quality of the mixture being formed.

In general, the noncondensable gas used in a steam-foam-forming mixture of the present invention can comprise substantially any gas which (a) undergoes little or no condensation at the temperatures and pressures at which the steam-foam-forming mixture is injected into and displaced through the reservoir to be treated and (b) is substantially inert to and compatible with the foam-forming surfactant and other components of that mixture. Such a gas is preferably nitrogen but can comprise other substantially inert gases, such as air, ethane, methane, flue gas, fuel gas, or the like. Preferred concentrations of noncondensable gas in the steam-foam mixture fall in the range of from about 0.0003 to 0.3 mole percent of the gas phase of the mixture. Concentrations of between about 0.001 and 0.2 mole percent are more preferred and concentrations between about 0.003 and 0.1 mole percent are considered most preferred.

In general, the electrolyte used should have a composition similar to and should be used in a proportion similar to those described as suitable alkali metal salt electrolytes in the '964 patent. The use of an aqueous solution containing an amount of electrolyte substantially equivalent in salting-out effect to a sodium chloride concentration of from about 0.1 to 5% (but less than enough to cause significant salting out) of the liquid phase of the steam is preferred.

As expressed in the '964 patent, the presence in the steam-foam-forming mixture of an electrolyte substantially enhances the formation of a foam characterized by a high degree of mobility reduction and a low interfacial tension. Some or all of the electrolyte can comprise an inorganic salt, preferably an alkali metal salt, more preferably an alkali metal halide, and most preferably sodium chloride. Other inorganic salts, for example, halides, sulfonates, carbonates, nitrates and phosphates, in the form of salts of alkaline earth metals, can be used.

Preference may be generally stated for an electrolyte concentration which has approximately the same effect on mobility reduction of the foam as does a sodium chloride concentration of between about 0.1 and 5 percent by weight (but less than a salting out-inducing proportion) of the liquid phase of the steam-foam-forming mixture. More preferably, the electrolyte concentration is between 0.1 and 5 percent, calculated on the same basis. Most preferably, the liquid phase of the steam-foam-forming mixture contains between about 1 and 4 percent by weight electrolyte. Further preference may generally be stated, in steam-foam compositions which contain electrolyte, for a weight ratio of electrolyte to surfactant which is in the range of from about 0.5 to 6; more preferably this ratio is in the range of from about 1 to 4.

In compounding a steam-foam-forming mixture or composition in accordance with the present invention, the steam can be generated by means of substantially any of the commercially available devices and techniques for steam generation. A stream of the steam being injection into a reservoir is preferably generated and mixed, in substantially any surface or downhole location, with selected proportions of substantially noncondensable gas, aqueous electrolyte solution, and foam-forming surfactant. For example, in such a mixture, the quality of the steam which is generated and the concentration of the electrolyte and surfactant-containing aqueous liquid with which it is mixed are preferably arranged so that (1) the proportion of aqueous liquid mixed with the dry steam which is injected into the reservoir is sufficient to provide a steam-containing fluid having a steam quality of from about 10-90% (and preferably from about 30-80%); (2) the weight proportion of surfactant dissolved or dispersed in that aqueous liquid is from about 0.01 to 5.0 (and preferably from about 1.0 to 4.0); and (4) the amount of noncondensable gas is from about 0.0003 to 0.3 mole fraction of the gas-phase of the mixture.

It will be observed, in this regard, that either or both of the optional electrolyte and noncondensable gas components might be, to some extent, supplied by the reservoir itself and thus the total supply thereof by surface facilities may not be necessary to the formation of steam-foams in which they are present. However, for best control over steam-foam composition and drive process performance, substantially all of each of the desired components of the steam-foam-forming mixture are injected along with the steam. Devices suitable for the mixing and injecting of steam-foam-forming mixtures for purposes of this invention are known to the art and commercially available.

In general, the steam can be suitably mixed with the noncondensable gas, electrolyte, and surfactant upstream of the reservoir, with or without a mixing and/or foam-forming device. The devices and techniques by which this is effected can comprise substantially any of those which are currently commercially available.

In a preferred correlation of the composition of the steam-foam-forming mixture with the properties of the rocks and fluid within the reservoir, consideration should be given to the selected extent of reduction which is desirable in the mobility of the steam within the reservoir when a steam channel has been formed and the oil saturation within that channel has been reduced to near a steam residual saturation. Such a correlation can indicate the pressure gradient best suited for injecting a given steam-foam-forming mixture and the foam it forms or comprises into such a steam channel at a a suitable rate of flow. The formulation needed for this can be found or verified by lab-testing an upflow of a selected steam-foam-forming mixture through a porous medium having an oil and water content at least substantially equivalent to those expected in the steam channel which is expected to form within the reservoir. The composition of the steam-foam-forming mixture should be adjusted to the extent required to provide a pressure gradient which exceeds that required for steam along but does not require an injection pressure which is likely to fracture the reservoir.

As known to those skilled in the art, the obtaining of the data pertinent to the oil saturations, temperatures and permeabilities to be expected within the reservoir can utilize data from numerous well logging, or the like measurements, core analyses, tests of reservoir fluids, and the like. Such determinations can also be conducted (or verified) by means of relatively simple laboratory tests, e.g., the presently described laboratory tests of steam-foam-forming properties of various steam-foam-forming surfactant systems within sand packs.

In a preferred procedure a determination is made of the injection pressure required for upflowing a steam-containing fluid of selected steam quality through a sand pack simulating the steam channel to be formed within the reservoir. A steam-foam-forming mixture is formed in accordance with the present invention and is flowed through the pack at a rate equivalent to the rate to be employed within the portion of the reservoir immediately surrounding an injection well. A determination is preferably made of the injection pressure and the effects of at least one change in the mobility of that steam-foam-forming mixture. The mobility change is preferably effected by increasing or decreasing the concentration of the surfactant and/or electrolyte in the steam-foam-forming mixture.

In general, the types of reservoirs to be treated and types of viscous oil production situations to which the present process is applicable are those described in the '964 patent. Preferably, the oil has a relatively high effective viscosity at the reservoir temperature. And, the reservoir is preferably sufficiently free of stratifications (due to differences in the absolute permeabilities of individual layers of rock) so that a significant proportion of an injected steam in not confined within only one or a few layers of rocks having an exceptionally high absolute permeability.

PERMEABILITY REDUCTION FACTOR DETERMINATION

The apparatus shown in FIG. 1 was used to provide an Ottawa sand pack having a porosity of 33.7%, a pore volume of 124 ml and an oil saturation of 30% PV of Kern River crude. Laboratory and field tests have indicated that permeability reduction factors measured with a permeable porous medium containing Kern River crude are relatively reliable indicators of how well a given steam-foam-forming mixture will perform. For example, if a given mixture is capable of providing a permeability reduction factor of less than 0.18 in a permeable porous medium containing Kern River crude, it is likely to be capable of providing an economically desirable reduction of steam-mobility within any reservoir containing an oil of similar viscosity and steam-foam-debilitating properties.

A typical steam-foam-forming composition which was tested for permeability reduction factor amounted to a substantially 50% quality steam containing 0.5% weight Siponate A-168 surfactant and 3.0% weight NaCl in its liquid-phase and 0.006 mole fraction of nitrogen in its gas-phase. In forming that composition, a stream of substantially dry steam was generated and injected by pumping water through a steam generator at 1.63 ml per minute. Streams of aqueous liquids containing, respectively, surfactant and brine were injected at, respectively, 0.78 ml/min and 0.84 ml/min. The nitrogen was injected at the rate of 12 std ml/min.

The steam permeability, $K_{SOR}$, was determined from the pressures, $P_1$ and $P_2$ (measured at locations 1 and 2 on FIG. 1), in accordance with the formula:

$$K = \frac{1094.6 \times L \times Q_W \times D_W \times V_S \times T}{A \times (P_2^2 - P_1^2)}$$

where:
$Q_w$ = mass flow of the water (cc/sec)
$D_w$ = Density of the water (g/cc)
$V_s$ = Viscosity of the steam (CP)
L = Length between the measuring locations (CM)
A = Cross-sectional area of the pack (CM)$^2$
T = Temperature ° F. above absolute zero (Rankine)
$P_2$ = Pressure at tap 2 (psig)
$P_1$ = Pressure at tap 1 (psig)
and:

$$K_{SOR} = \frac{1094.6 \times 11.38 \times 0.0272 \times 0.997 \times 001306 \times 702}{12.65 \times 454}$$

and:

$$K_{SOR} = 0.539 \text{ darcy}$$

The permeability to the steam-foam-forming composition, $K_F$, was determined similarly, with the terms of the formula becoming:

$$K_F = \frac{1094.6 \times 11.38 \times 0.0272 \times 0.997 \times 0.01512 \times 819}{12.65 \times 15470}$$

$$K_F = 0.021 \text{ darcy}$$

Thus, the permeability reduction factor, $K_F/K_{SOR}$, was found to be:

$$\frac{K_F}{K_{SOR}} = \frac{0.021}{0.539} = 0.039$$

What is claimed is:
1. A process for testing the steam mobility-reducing capability of an olefin sulfonate-containing surfactant formulation for reducing the mobility of steam of a selected quality within a selected subterranean oil-containing reservoir, comprising:
comparing steam of the selected quality with a steam-containing fluid which has substantially the same steam quality but contains said surfactant formulation, an electrolyte and a noncondensable gas in proportions which are at least near optimum for steam foam formation by upflowing the fluids being compared through columns of permeable porous mediums containing the reservoir oil, or an oil of substantially equivalent viscosity and steam-foam-debilitating properties, at mass flow rates which are substantially equivalent to a selected flow rate suitable for use in the near-well portion of the reservoir;

measuring the steady-state pressures developed within said columns at internal locations which are substantially free of end effects; and utilizing the measured pressures to calculate the permeability reduction factor of said surfactant formulation.

2. The process of claim 1 in which the chemical composition of said olefin sulfonate-containing surfactant formulation is adjusted to the extent required to make it capable of providing, in such a test, a permeability reduction factor of less than about 0.18.

* * * * *